(12) United States Patent
Song et al.

(10) Patent No.: US 12,029,447 B2
(45) Date of Patent: Jul. 9, 2024

(54) LAPAROSCOPIC SURGERY SUPPORT SYSTEM

(71) Applicant: University of Central Florida Research Foundation, Inc., Orlando, FL (US)

(72) Inventors: Sang-Eun Song, Orlando, FL (US); Eric Barker, Orlando, FL (US); Israel Camacho, Apopka, FL (US); Tanner Drake, Orlando, FL (US); Immanuel Girgis, Wellington, FL (US); Matthew Hook, Land O Lakes, FL (US); Karina Thomas, Green Cove Springs, FL (US); Alex Zaffos, Cooper City, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 193 days.

(21) Appl. No.: 17/351,177

(22) Filed: Jun. 17, 2021

(65) Prior Publication Data
US 2021/0393289 A1    Dec. 23, 2021

Related U.S. Application Data

(60) Provisional application No. 63/042,346, filed on Jun. 22, 2020.

(51) Int. Cl.
*A61B 17/34*    (2006.01)
*A61B 17/00*    (2006.01)
*A61B 90/50*    (2016.01)

(52) U.S. Cl.
CPC .......... *A61B 17/3423* (2013.01); *A61B 90/50* (2016.02); *A61B 2017/00973* (2013.01); *A61B 2017/3445* (2013.01); *A61B 2017/3492* (2013.01)

(58) Field of Classification Search
CPC .............. A61B 17/3423; A61B 90/50; A61B 2017/00973; A61B 2017/3492
See application file for complete search history.

(56) References Cited

U.S. PATENT DOCUMENTS

| | | | | |
|---|---|---|---|---|
| 5,597,146 | A * | 1/1997 | Putman | A61B 90/50 248/176.2 |
| 5,626,595 | A * | 5/1997 | Sklar | A61B 17/320016 606/180 |
| 6,579,281 | B2 * | 6/2003 | Palmer | A61B 17/3421 606/1 |

(Continued)

OTHER PUBLICATIONS

Embury, Robert, "Tensile Testing Results of Toner Plastics 3D Filament". (Dec. 12, 2019). Retrieved from https://toner-plastics.com/tesile-testing-results-of-toner-plastics-3d-filament/.

(Continued)

*Primary Examiner* — Zade Coley
*Assistant Examiner* — Diana Jones
(74) *Attorney, Agent, or Firm* — Locke Lord LLP; Nicholas J. DiCeglie, Jr.

(57) ABSTRACT

A laparoscopic surgery support system can include a plurality of ports configured to receive a trocar therethrough and a plurality of arms connecting the plurality of ports together and configured to allow fixation of a relative position of the plurality of ports. For example, the plurality of ports can include three or more ports.

15 Claims, 9 Drawing Sheets

(56) References Cited

U.S. PATENT DOCUMENTS

| | | | |
|---|---|---|---|
| 6,582,420 B2 | 6/2003 | Castaneda et al. | |
| 9,125,662 B2 | 9/2015 | Shelton, IV | |
| 2011/0071541 A1* | 3/2011 | Prisco | A61B 34/37 |
| | | | 606/130 |
| 2013/0041219 A1* | 2/2013 | Hasegawa | A61B 17/29 |
| | | | 600/109 |
| 2017/0156808 A1* | 6/2017 | Auld | A61B 34/70 |
| 2018/0168689 A1* | 6/2018 | Beckman | A61B 90/50 |
| 2018/0168746 A1* | 6/2018 | Swayze | A61B 17/3423 |

OTHER PUBLICATIONS

Reich, H., Ribeiro, S. C., Rasmussen, C., Rosenberg, J., & Vidali, A. (1999). "High-pressure trocar insertion technique". Retrieved Apr. 16, 2020, from https://www.ncbi.nlm.nih.gov/pmc/articles/PMC3015333/.

Cantrell, J., Rohde, S., Damiani, D., Gurnani, R., DiSandro, L., Anton, J., Andie Young. (Jan. 1, 1970). "Experimental Characterization of the Mechanical Properties of 3D Printed ABS and Polycarbonate Parts". Retrieved Apr. 16, 2020, from https://link.springer.com/chapter/10.1007/978-3-319-41600-7_11.

Wojtyla, S., Klama, P., & Baran, T. (2017)."Is 3D printing safe? Analysis of the thermal treatment of thermoplastics": ABS, PLA, PET, and nylon. Journal of Occupational and Environmental Hygiene, 14(6), D80-D85. https://doi.org/10.1080/15459624.2017.1285489.

Studies from Colorado State University Reveal New Findings on Veterinary Surgery "Laparoscopic Entry Techniques: What Is the Controversy". VeterinaryWeek. https://search-ebscohost com.ezproxy.net.ucf.edu/login.aspxdirect=true&db=edsgao&AN=edsgcl.589278563&site=eds-live&scope=site. Published 2019. Accessed Oct. 5, 2019.

Utpal De. View Point—"Ergonomics and laparoscopy". 2005. https://search.ebscohost.com/login.aspxdirect=true&db=edsbas&AN=edsbas.251BA6CB&site=eds-live&scope=site. Accessed Oct. 4, 2019.

Cullinan DR, Schill MR, DeClue A, Salles A, Wise PE, Awad MM. "Fundamentals of Laparoscopic Surgery: Not Only for Senior Residents". J Surg Educ. 2017;74(6):e51-e54. doi: 10.1016/j.jsurg.2017.07.017.

Perugini RA, Callery MP. "Complications of laparoscopic surgery". In: Holzheimer RG, Mannick JA, editors. Surgical Treatment: Evidence-Based and Problem-Oriented. Munich: Zuckschwerdt; 2001. Available from: https://www.ncbi.hlm.nih.gov/books/NBK6923/.

Ali R, Anwar M, Akhtar J. "Laparoscopic versus open appendectomy in children: a randomized controlled trial from a developing country". Journal of Pediatric Surgery. 2018;53(2):247-249. doi:10.1016/j.jpedsurg.2017.11.022.

Jonsson B, Zethraeus N. "Costs and Benefits of Laparoscopic Surgery"—a Review of the Literature. European Journal of Surgery. 2000;166(12):48. doi:10.1080/110241500750056553.

Boggess, John F. "Robotic Surgery in Gynecologic Oncology: evolution of a new surgical paradigm", J Robotic Surg (2007) pp. 31-37.

Anderson et al., "Robot-like dexterity without computers and motors: a review of hand-held laparoscopic instruments with wrist-like tip articulation", Expert Rev Med Devices. Jul. 2016 ; 13(7): 661-672. doi:10.1586/17434440.2016.1146585.

Hale, Conor, "CMR unveils portable, modular Versius robotic surgery system", https://www.fiercebiotech.com/medtech/cmr unveilsportable modular versiusrobotic surgery system.

Moore, E. J. (n.d.). "Robotic surgery" Retrieved Oct. 5, 2019, from https://www.britannica.com/science/robotic-surgery.

Da Vinci by Intuitive. (n.d.). Retrieved Oct. 2, 2019, from https://www.intuitive.com/en-us/products-and-services/da-vinci.

* cited by examiner

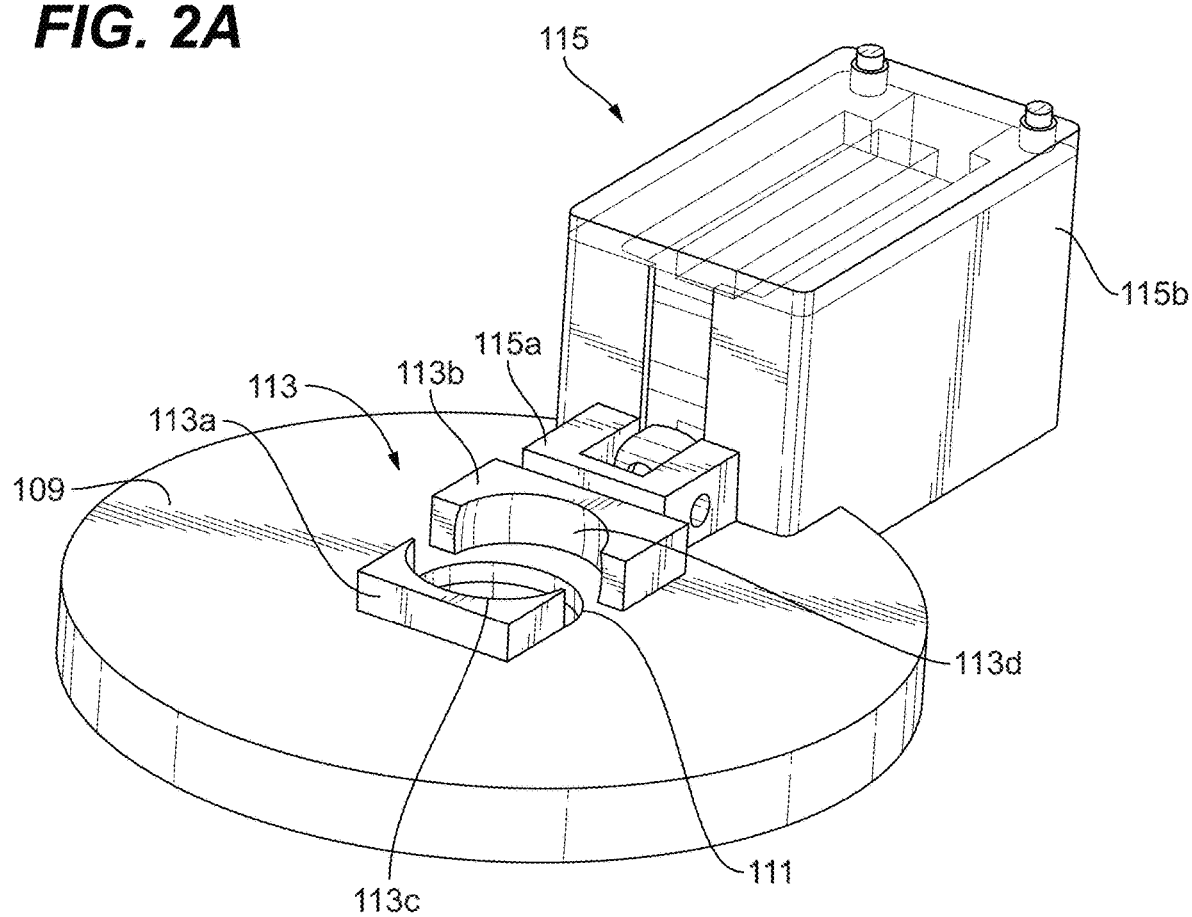

LAPAROSCOPIC SURGERY SUPPORT SYSTEM

CROSS-REFERENCE TO RELATED APPLICATIONS

This application claims priority to and the benefit of U.S. Provisional Application No. 63/042,346, filed Jun. 22, 2020, the entire contents of which are herein incorporated by reference in their entirety.

FIELD

This disclosure relates to laparoscopic surgery support system

BACKGROUND

Laparoscopy is a surgical method designed to be as minimally invasive as possible, compared to traditional open surgery. This benefits patients by decreasing scarring and recovery time, making the procedure the more favored option. In laparoscopic surgery, a hollow needle-tipped tube known as a trocar is inserted by making small incisions in the abdomen, acting as a port for inflating the work area and placing an endoscope and tools inside of the body. Standard laparoscopy tools can cut, cauterize, grab, and suture. However, they each require individual manipulation and holding so that the surgeon must continuously engage the tools during surgical tasks. In conventional laparoscopy, there is no device or utility given to hold tools at a position to pause surgeon's manipulation, which can cause stress, fatigue, irritation, etc., especially for longer procedures.

Robotic laparoscopy systems have been a great solution for such problems since surgeons can pause and disengage surgical tasks at any time. Some sophisticated surgical tasks can only be performed using such robots. However, many other simpler procedures, such robots provide simple functions i.e., remaining tool position when not manipulated by the surgeon, which can be achieved without a laparoscopy robot by adding a simple assistant system.

Many large hospitals are utilizing robots for laparoscopic surgery, such as the da Vinci Surgical System. The robotic system can hold tools in place while the surgeon is manipulating the other tools, and can be activated and deactivated through its control panel. Obvious downside to using such robots is that it is very costly and require a large designated space. The da Vinci Surgical System ranges between $1-$1.5 million, not including the cost of tools, training, and upkeep. In addition to that, robotic laparoscopic surgery is much slower than the traditional method as it requires additional steps for the robotic procedure.

Conventional laparoscopic surgery methods and systems have generally been considered satisfactory for their intended purpose. However, there is still a need in the art for improved laparoscopic surgery support systems. The present disclosure provides a solution for this need.

SUMMARY

A laparoscopic surgery support system can include a plurality of ports configured to receive a trocar therethrough and a plurality of arms connecting the plurality of ports together and configured to allow fixation of a relative position of the plurality of ports. For example, the plurality of ports can include three or more ports.

The plurality of arms can be multilink arms, for example. In certain embodiments, the multilink arms can include a holding force of about 10 kg or greater. Any other suitable arms are contemplated herein.

In certain embodiments, one or more (e.g., all) of the plurality of ports can be any suitable port, e.g., as disclosed herein (e.g., as described below). For example, in certain embodiments, one or more of the ports (e.g., all) can include a body, a trocar aperture defined through the body and configured to receive a trocar, and a brake configured to hold the trocar in a position relative to the body. The brake can be configured to be selectively engaged and disengaged by a user.

The system can include an input configured to receive a user command to actuate the brake to selective hold the trocar. For example, the input can be a foot pedal or a voice command device. Any other suitable input is contemplated herein.

The system can include one or more of the trocars configured to be engaged by the brake, e.g., as described below. Any suitable number and/or type of trocar is contemplated herein. In accordance with at least one aspect of this disclosure, a laparoscopic surgery port can include a body, a trocar aperture defined through the body and configured to receive a trocar, and a brake configured to hold the trocar in a position relative to the body. The brake can be configured to be selectively engaged and disengaged by a user. In certain embodiments, the brake can include a first clamp portion and a second clamp portion configured to compress a portion of the trocar.

In certain embodiments, the first clamp portion can be fixed to the body and the second clamp portion can be moveable relative to the body. In certain embodiments, the first clamp portion and the second clamp portion can be configured to compress a joint disposed on the trocar.

In certain embodiments, the port can include an electric motor configured to actuate the brake (e.g., when a command from a foot pedal is received). In certain embodiments, the brake can be mechanically activated.

In accordance with at least one aspect of this disclosure, a trocar can include a trocar tube and a joint connected to the trocar tube and configured to be compressed by a brake of a laparoscopic surgery port. The joint can include one or more radially outwardly extending slits extending from the trocar tube and configured to flex, for example. The joint can be shaped to create a ball and socket joint with the port to allow the trocar to rotate in the port such that the trocar can be positioned by a user to a desired insertion angle and/or subsequently held by the brake.

In accordance with at least one aspect of this disclosure, a method can include performing laparoscopic surgery with a system, port, or trocar as disclosed herein. The method can include locking a trocar in position using a brake. The method can include unlocking a trocar to move the trocar. The method can include any other suitable method(s) and/or portion(s) thereof.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 2A is a perspective view of an embodiment of a port in accordance with this disclosure, shown having an embodiment of an actuator connected thereto;

DETAILED DESCRIPTION

Figure 1A:
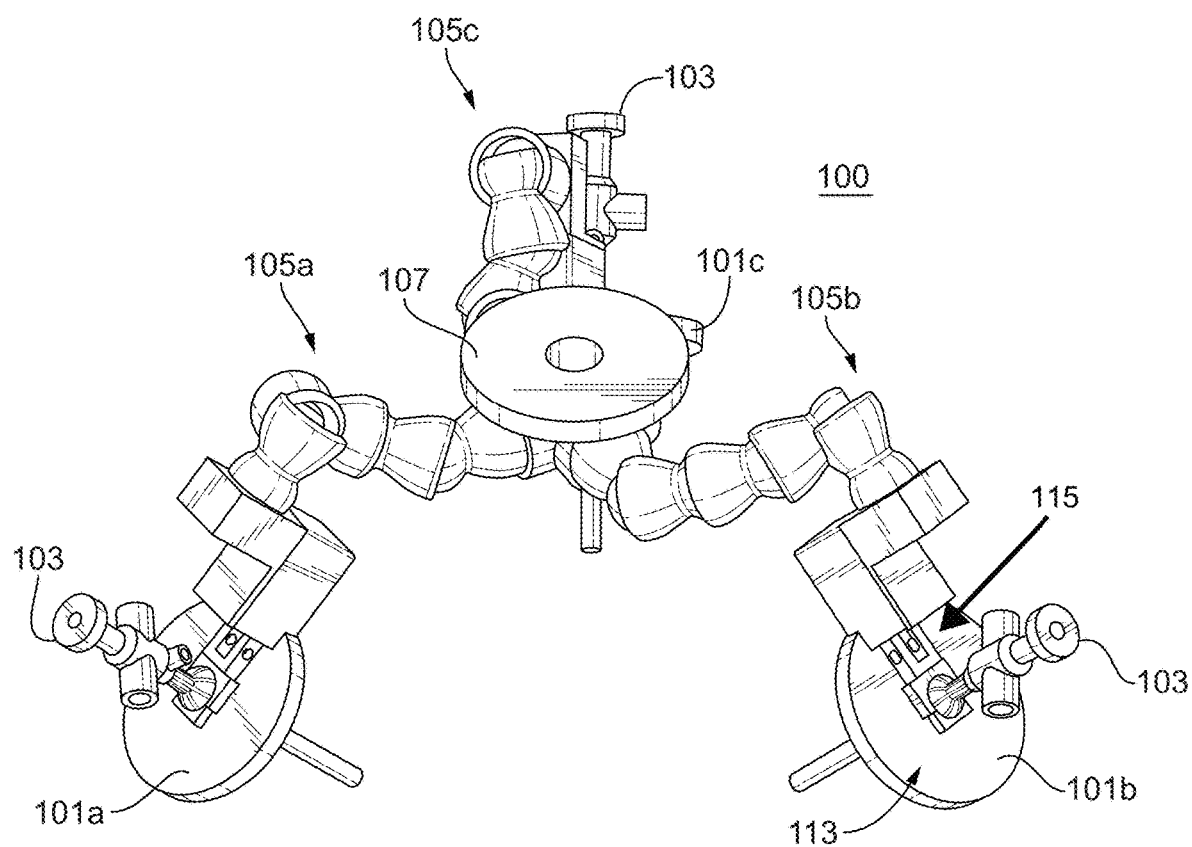
FIG. 1A is a perspective view of an embodiment of a system in accordance with this disclosure.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1A and is designated generally by reference character 100.

Other embodiments and/or aspects of this disclosure are shown in FIGS. 1B-4B.

Figure 1B:
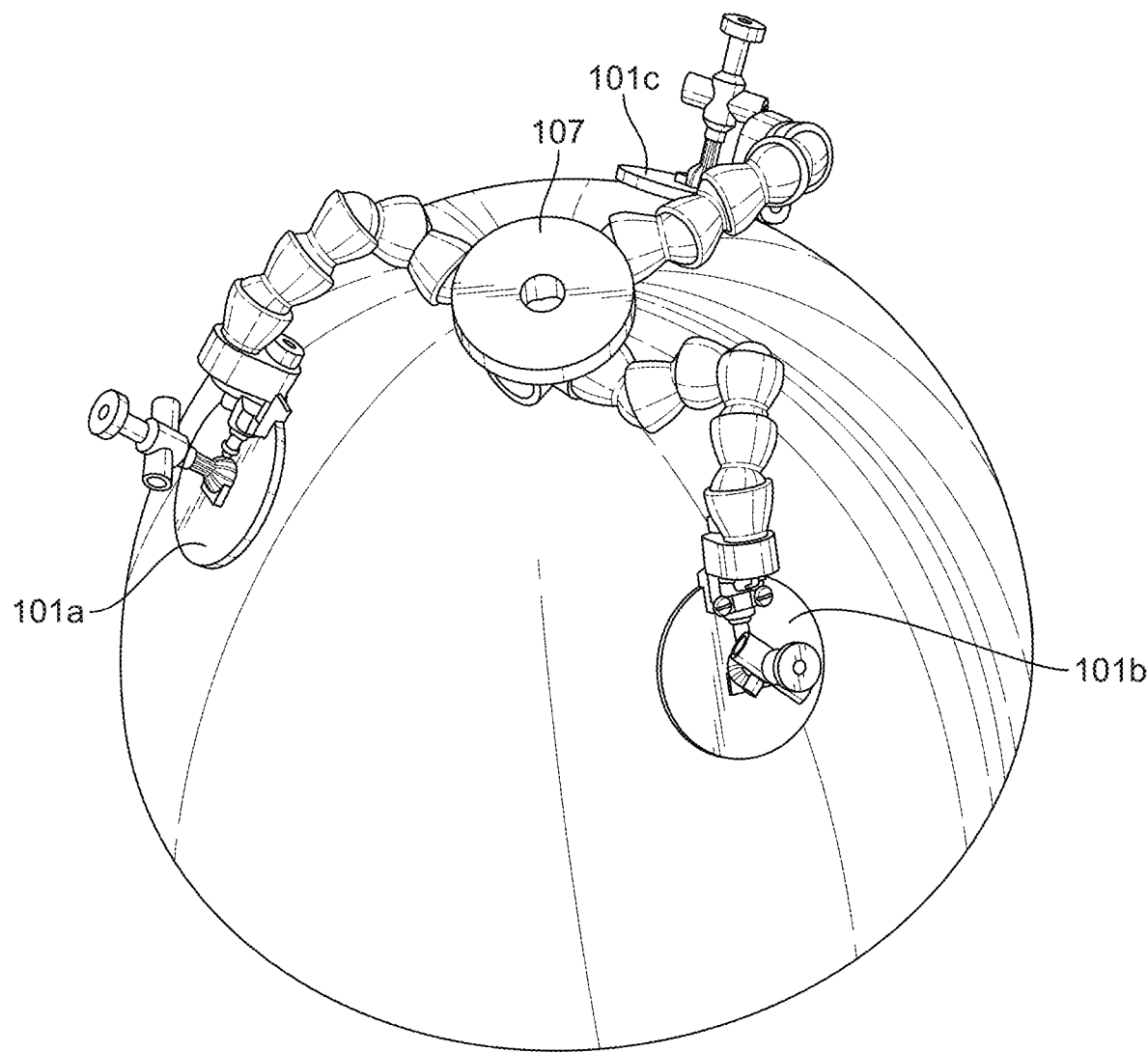
FIG. 1B is a perspective view of the embodiment of FIG. 1A, shown disposed on an insufflated abdomen and having a trocar inserted into each port thereof.

Referring to FIGS. 1A and 1B, a laparoscopic surgery support system 100 can include a plurality of ports 101a, 101b, 101c configured to receive a trocar 103 therethrough and a plurality of arms 105a, 105b, 105c connecting the plurality of ports 101a, b, c together. The plurality of arms 105a, b, c can be configured to allow fixation of a relative position of the plurality of ports 101a, b, c. For example, the plurality of ports 101a, b, c can include three or more ports 101a, b, c (e.g., three as shown). Each of the plurality of ports 101a, b, c can be configured for use in laparoscopic surgery.

The plurality of arms 105a, b, c can be multilink arms as shown, for example (e.g., such as GorillaPod™ arms). For example, the multilink arms 105a, b, c can include a plurality of links jointed together (e.g., in a ball and socket type joint) and providing a certain resistance to motion (e.g., based on the tightness of fit between each link in a subsequent link). In certain embodiments, the arms 105a, b, c can include a holding force (e.g., at a distal end) of about 10 kg or greater such that the arms or links thereof do not move unless such a force or greater is applied thereto. Any other suitable arms or types thereof are contemplated herein.

The multilink arms 105a, b, c can be joined together at a center member 107 which can be free floating and/or can be attached to an external structure (e.g., a surgical table) to hold the position of all arms 105a, b, c in 3D space. Any suitable arms that can be locked into position (e.g., with a lever lock) or that provide sufficient resistance to prevent motion thereof in surgery are contemplated herein, for example.

Certain embodiments can include multilink arms 105a, b c, which can include a medical grade lever lock that locks arms into a position, for example. In certain embodiments, the arms may have a maximum force design for allowing motion of ports relative to each other (e.g., for safety and FDA rule compliance). Certain multilink arms commercially available such as those sold under the trademark GorillaPod™, for example, can be used (e.g., which can have a 10 kg normal holding force, but will move with sufficient force to prevent potential damage). Embodiments can include three or more arms for mounting to abdomen, for example.

Figure 2B:
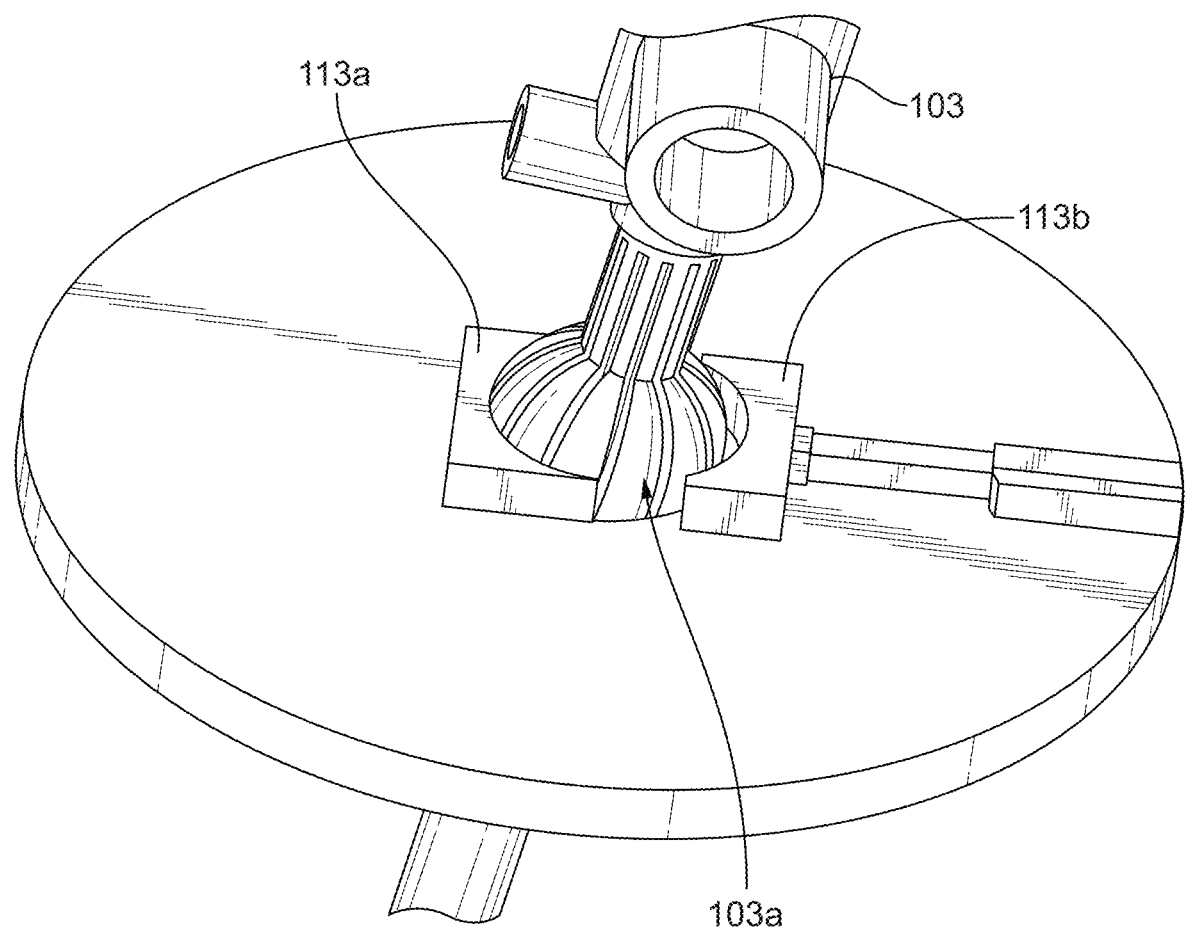
FIG. 2B is a perspective view of an embodiment of a port in accordance with this disclosure, shown having an embodiment of a trocar disposed therein.
Figure 2C:
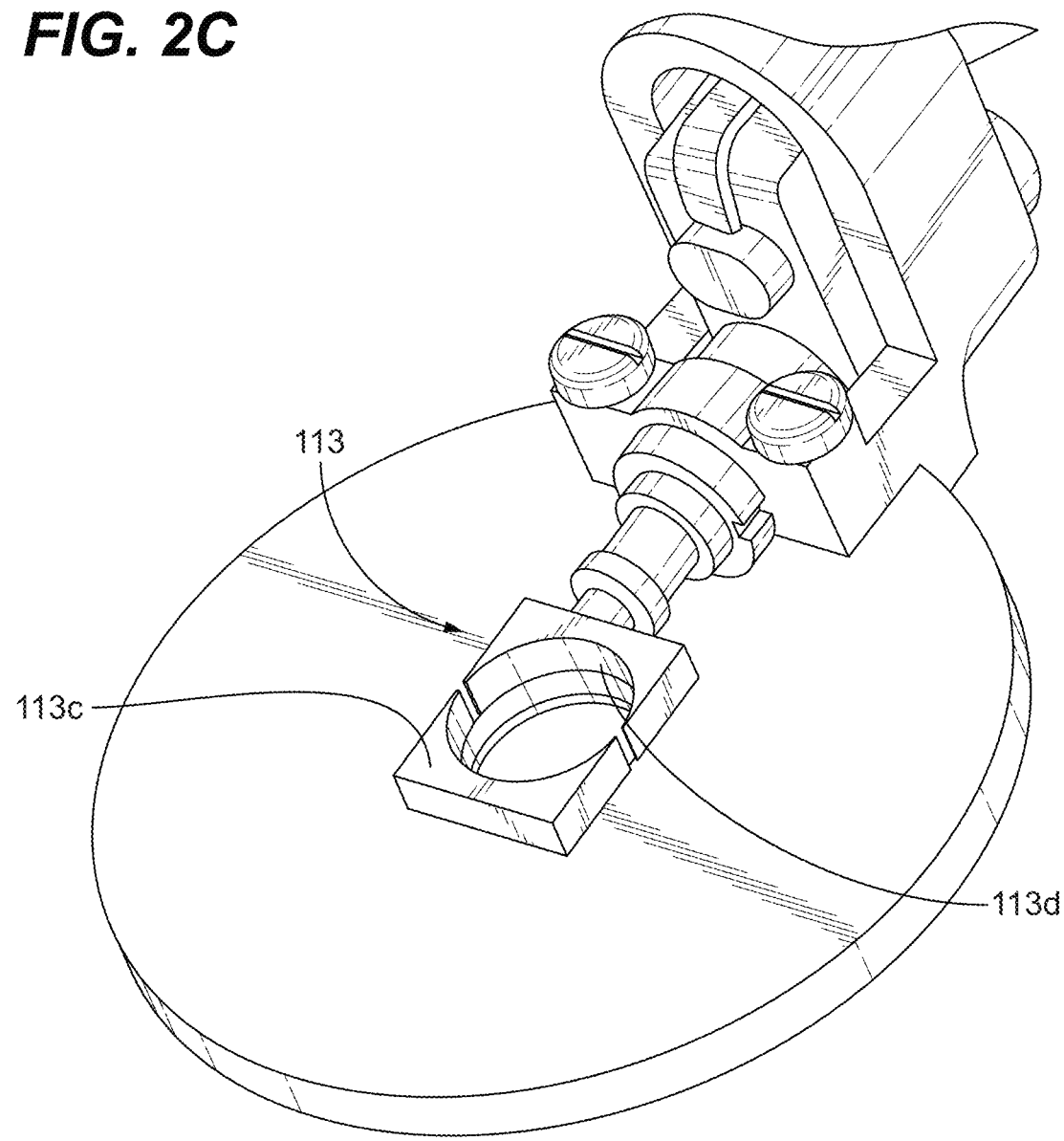
FIG. 2C is a perspective view of an embodiment of a port in accordance with this disclosure, shown having an embodiment of an actuator connected thereto.

Referring additionally to FIGS. 2A-2C, in certain embodiments, one or more (e.g., all) of the plurality of ports 101a, b, c as disclosed herein (e.g., as described below). For example, in certain embodiments, one or more of the ports 101a, b, c (e.g., all) can include a body 109, a trocar aperture 111 defined through the body 109 that is configured to receive a trocar 103 (e.g., shown in FIG. 2B with trocar disposed therein). The body 109 of the ports 101a, b, c can include any suitable shape. For example, the body 109 can be a disk (e.g., forming a port disk), e.g., as shown, or can be any suitable shape or structure. The body 109 can be a single piece and/or include one or more detachable/movable pieces (e.g., connected via a hinge) to allow the body to be placed around a trocar 103, e.g., after insertion.

The one or more ports 101a, b, c can also include a brake 113 configured to hold the trocar 103 (e.g., as shown in more detail in FIGS. 3A and 3B) in a position relative to the body 109. The brake 113 can be configured to be selectively engaged and disengaged by a user. In certain embodiments, the brake 113 can include a first clamp portion 113a and a second clamp portion 113b configured to compress a portion of the trocar 103. In certain embodiments, the first clamp portion 113a can be fixed to the body 109, e.g., as shown, and the second clamp portion 113b can be moveable relative to the body 109 (e.g., to slide relative to the surface of the body 109). For example, the second clamp portion 113b can be attached to an actuator 115 (e.g., to a linear motion arm 115a of the actuator 115) to be moved by the actuator 115 (e.g., linearly toward the trocar opening 111). Any suitable actuator structure and/or actuator arm structure is contemplated herein (e.g., as shown in FIGS. 2A-2C). Any mechanical connection between the second clamp portion 113b and the actuator 115 is contemplated herein. Any suitable connection or housing (e.g., housing 115b as shown in FIG. 2B) for the actuator 115 to connect to the one or more arms 105a, b, c is contemplated herein.

In certain embodiments, each port 101a, b, c can include an actuator 115. Each actuator 115 can include an electric motor (e.g., disposed inside the actuator housing 115b) configured to actuate the brake 113 (e.g., when a command from a foot pedal is received, e.g., as further described below). Each actuator 115 can be electrically connected to an input device or other suitable controller to selectively operate each electric motor.

In certain embodiments, the brake 113 can be mechanically activated (e.g., manually with mechanical linkages, wires, rods, buttons, levers, etc.). As disclosed above, the brake 113 can be mechanical and/or electromechanical, and/or controlled in any suitable manner, e.g., wireless, wired, mechanical linkage, etc.

Figure 4A:
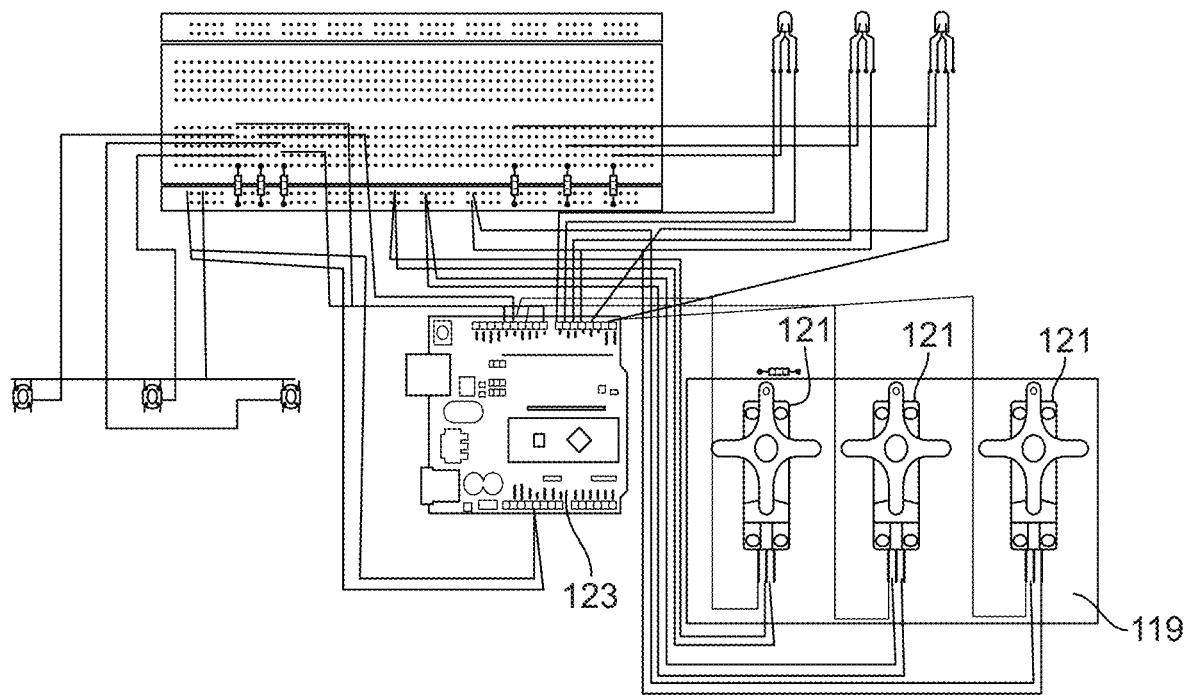
FIG. 4A is a schematic diagram of an embodiment of a brake control system in accordance with this disclosure.
Figure 4B:
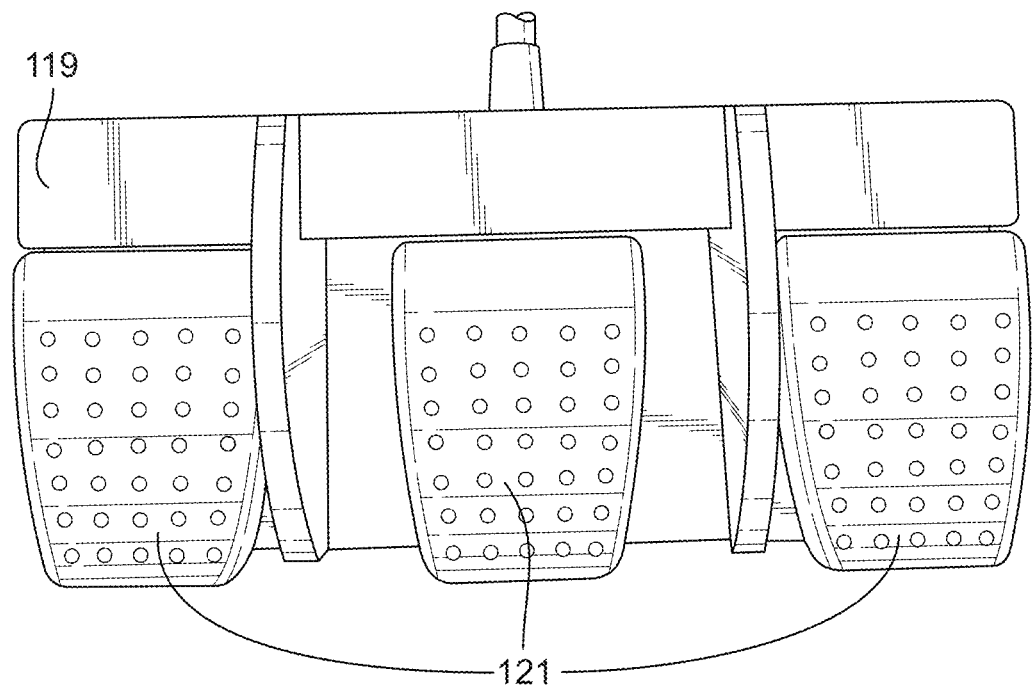
FIG. 4B is a perspective view of an embodiment of a foot pedal assembly for the brake control system of FIG. 4A.

Each brake 113 (e.g., each actuator 115) of each port 101a, b, c can be configured to be operated independently of each other and/or can be configured to operate together (e.g., such that a single input controls all brakes). For example, referring additionally to FIGS. 4A and 4B, the system 100 can include an input 119 configured to receive a user command to actuate one or more (e.g., each) of the brakes 113 to selectively hold the trocar 103. For example, the input 119 can be a foot pedal 121 or a voice command device. Any other suitable input (e.g., a button) is contemplated herein. Embodiments can include a light or other suitable indicator, e.g., as shown, to indicate the brake 113 is in the locked position and/or unlocked position. Referring to FIGS. 4A and 4B, certain embodiments can include a separate foot pedal 121 for each brake 113 to independently control braking of each trocar 103, for example. An embodiment of a complete circuit diagram of all the wiring can be seen in FIG. 4A.

Certain embodiments can include a control module 123 configured to determine whether an input 119 is being actuated and to control locking or unlocking (e.g., toggle lock/unlock) and/or to indicate which state each brake 113. The control module 123 can include any suitable hardware and/or software module(s) configured to perform any suitable function, e.g., as disclosed herein.

Any suitable actuator housings are contemplated herein. Embodiments can be configured to provide easy accessibility of the actuators that to allow for either maintenance or replacement, for example. An embodiment of an actuator assembly can include a custom base and cover that properly accommodates the actuator and is held in place by two sliding retainers.

In certain embodiments, referring to FIG. 2B, the first clamp portion 113a and the second clamp portion 113b can be configured to compress a joint 103a disposed on the trocar 103. For example, as shown, the first clamp portion 113a and the second clamp portion 113b can include a semi-circular inner surface 113c, 113d configured to partially conform to and press against the joint 103a (e.g., having a ball joint shape, e.g., as described further below). Any other suitable shape for the first clamp portion 113a and the second clamp portion 113b is contemplated herein. Any other suitable brake assembly is also contemplated herein.

The system 100 can include one or more of the trocars configured to be engaged by the brake 113, e.g., as described below. Any suitable number and/or type of trocar is contemplated herein.

Figure 3A:
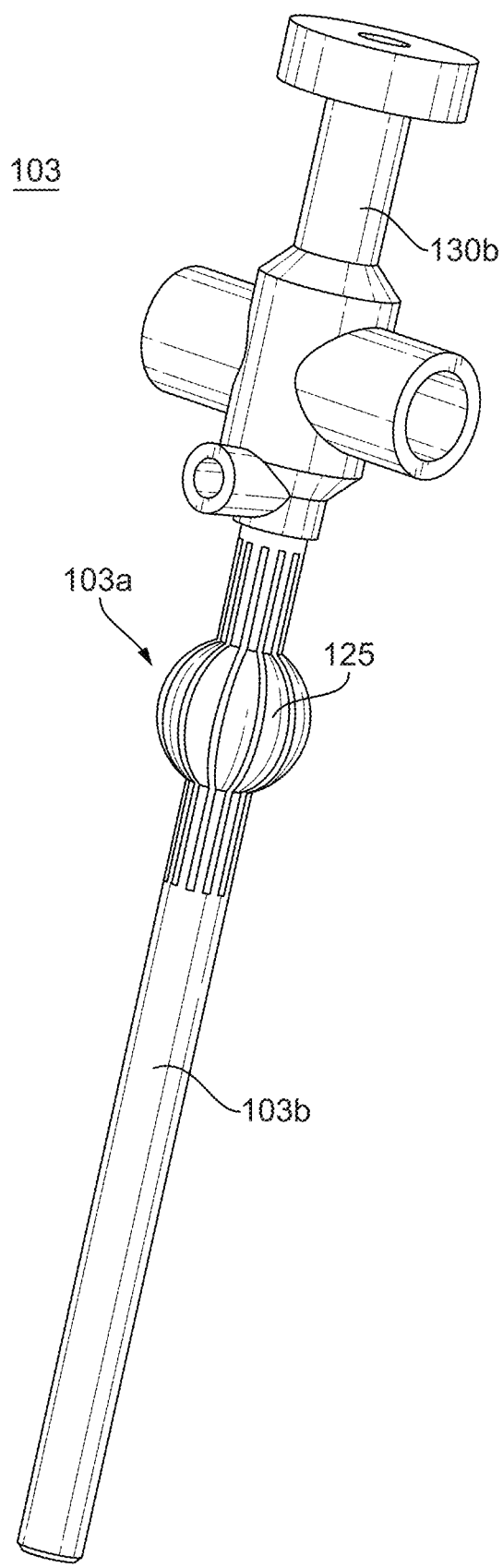
FIG. 3A is a perspective view of an embodiment of a trocar in accordance with this disclosure.

Referring additionally to FIG. 3A, in accordance with at least one aspect of this disclosure, a trocar 103 can include a trocar tube 103b and a joint 103a connected to the trocar tube 103b and configured to be compressed by a brake 113 of a laparoscopic surgery port (e.g., ports 101a, b, c). The joint 103a can include one or more radially outwardly extending slits 125 (e.g., defined longitudinally) extending from the trocar tube 103b and configured to flex, for example. The joint 103a can be shaped to create a ball and socket joint with the port 101a, 101b, 101c to allow the trocar 103 to rotate in the port 101a, b, c such that the trocar 103 can be positioned by a user to a desired insertion angle and/or subsequently held by the brake 113. Any suitable portion of the trocar tube 103b and/or joint 103a can be weakened, e.g., by slits, to allow compression of the material, e.g., by a brake 113.

As described above, embodiments can include a trocar that has a joint formed thereon or attached thereto. The joint can be spherical or any suitable shape to create a suitable movable joint, for example. In certain embodiments, e.g., as shown, the joint (and part of the cannula on both proximal and distal side of joint in certain embodiments) can have vertical slits (or other suitable weakened areas) to make the joint flexible and compressible by push brake, for example. Embodiments of a trocar can include an inner straw inside the cannula of the trocar to make an air/water tight fluid path inside, while having a slit and flexible joint on the outside.

In accordance with at least one aspect of this disclosure, a method can include performing laparoscopic surgery with a system, port, or trocar as disclosed herein. The method can include locking a trocar in position using a brake. The method can include unlocking a trocar to move the trocar. The method can include any other suitable method(s) and/or portion(s) thereof.

In certain embodiments, one or more trocars can be inserted into a patient's body first, and then the ports can be placed over trocar (e.g., disks that are split in half, e.g., hinged together to clamp around trocar spherical joint). In certain embodiments, the trocar aperture can be too small for the trocar joint to pass through (e.g., the joint can have a large diameter than the trocar aperture), which can limit motion into and out of abdomen and/or the port. In certain embodiments, when disposed in the trocar aperture of the port, the trocar and joint may interact in a way that only allows rotation.

Embodiments include a laparoscopy support system that bridges the gap between manual and robotic laparoscopy. Embodiments can be semi-robotic in such a way that the tools can still be manipulated by the surgeon with their own speed and precision, however, the surgeon can lock position and rotation of each trocar and inserted tool in place using a controller e.g., a foot pedal. Embodiments can provide the surgeon with the capability to hold laparoscopy tools during surgical tasks, which can only be provided when using robotic system.

FIG. 1A shows an example of an embodiment of a system providing a fixed workspace. The system can include multiple ports (e.g., ports as shown in FIG. 2A), through where a specially designed trocar (e.g., as shown in FIG. 3A) can be inserted. As shown, the port can include a disk body. These discs can be mechanically connected (which can be a locking mechanism or a heavy duty flexible arms like a Gorilla tripod) shown as in FIG. 1A. By having multiple ports connected, the surgical space can become a fixed coordinate system like robotic laparoscopy. Endoscopic camera view and handling laparoscopy tools can be far stable and intuitive unlike conventional laparoscopy that all components are independent. The system can surround an inflated abdomen at least three widely spread entry locations so that it will not be easily dislocated by typical laparoscopy tool manipulations. For added safety, the overall structure can be held by a fixation arm (e.g., at the connection point of all arms, shown as a top disc in FIG. 1A) that can be attached from side rail of standard operating tables. Embodiments can include a push brake configured for pressing trocar spherical joint.

Embodiments can also hold a laparoscopic tool inserted through the trocar. As shown in FIG. 2A, a locking mechanism can be featured on the disc that can halt the remote center of motion (RCM) movement of the trocar as well as the movement (in-and-out and axial turn) of the tool inserted inside. Overall, a single locking can pause the trocar and tool at all degrees-of-freedom. The locking mechanism can be an electric motor that can press the special joint of the trocar, which can be controlled by various methods such as foot pedal (assuming surgeon's both hands are engaged with tools or voice control). Both trocars can be locked and released together or individually as needed.

Embodiments of a trocar can include a spherical joint that can be used as a brake for both trocar itself and the tool inside the trocar, for example. The trocar can include a spherical shape incorporated into the trocar that can be compressed to clamp both the tool and trocar in place. The slots shown can allow the sphere to be flexible enough to be pressed. The trocar design can have open slots around the joint unlike sealed trocar, which is air and liquid tight. In certain embodiments, a semi flexible inner sheath can be added in the cannula to provide sealing.

Embodiments provide reduced cost, increased operational simplicity requiring less facility/space/staff, and mobility making it possible to use in non-equipped operating rooms, e.g., for the military. In general, embodiments can reduce the strain on the patient due to decreased surgery time and a higher precision of tool manipulation, due to the ability to suspend the tools in their individual configurations. Additionally, embodiments can require less manpower in the operating room which in turn leads to less clutter. In certain embodiments, laparoscopic tools inserted through the trocar can be braked in all motions, e.g., axial rotation and in-and-out motion. This allows the user to freeze a laparoscopic tool(s) which is the main function of the system.

When specifically comparing to traditional laparoscopy, embodiments surpass current methods by providing more control, e.g., lock and release, a more stable workspace, comparable speed and simplicity, and reduced risk of human error. For example, incidents of sharp tips of laparoscopic tools damaging tissue when not held properly, out of endoscopic view, or due to unwanted accidental movement can be eliminated or reduced by utilizing embodiments having a brake system and fixed port location/angle. When specifically comparing to traditional robotic laparoscopic surgery, embodiments are less expensive, do not require a special facility or space, are less complex and more time efficient, and do not require user training.

Embodiments can be used for any conventional laparoscopic surgery. Embodiments can replace costly robotic laparoscopic surgery depending on procedures. The system can be particularly useful in non-equipped operating room setups, e.g., military field operation. In certain embodiments, any electrical operation can be powered from typical power outlet and/or a battery that allows field operation (e.g., for military use) and/or emergency operation in case of power outage. Certain embodiments can also be used without power, e.g., with non-electrical mechanical locking and braking. If used with a portable endoscopic camera, this operation can be performed in any less equipped environment. Certain embodiments can be attached to operating room table to increase structural stability.

There is currently no cost effective options between high cost robotic surgery and conventional laparoscopy. Embodiments can provide critical assisting functions with affordable costs. Also, embodiments can be portable so no additional facility is needed, unlike robotic surgery setup.

As appreciated by one having ordinary skill in the art, the system can include any suitable control module(s) (e.g., for receiving input signals and/or causing actuation of the brake). The control module(s) can include any suitable hardware and/or software module(s) configured to perform the associated function, e.g., as disclosed below.

Embodiments can include a semi-robotic laparoscopic tool support system. Traditional laparoscopy is a method of surgery that consists of using several tools inserted in small incisions in the body while a surgeon uses a small camera to view the inside of the patient. It allows for smaller incisions, quicker healing time, and less risk of infection. Currently, the most advanced form of laparoscopic surgery involves using a robot to perform the manual operations while controlled by the surgeon. It is very precise but exponentially more expensive than traditional laparoscopic surgery. There is no intermediary device between traditional laparoscopic surgery and robot-supported solutions. In conventional laparoscopy, surgeons have no convenient method of fixing the tools' orientations and robotic systems are often not practical due to time and monetary constraints. Embodiments can improve upon conventional laparoscopy by adding a support system to fix tools in desired orientations in a cost effective manner.

Laparoscopic surgery is a form of minimally-invasive surgery that has benefitted both patients and surgeons. It has allowed surgeons to perform surgeries like appendectomies and hysterectomies from the inside of the patient to forego creating a large scar. It minimizes blood loss and accelerates the recovery time. While it is very advantageous, it lacks key components that would maximize the efficiency of the procedure. This method requires several assistants to help by holding tools in place while not in use. The surgeon is not able to proceed alone and requires the assistance of others in order to change any movement of the tools. This allows for human errors to be made, as it is impossible to physically hold an item without moving. Conversely, some medical centers use a robot, such as the da Vinci Surgical System, to aid in these procedures. While it is very precise, it is also very expensive and takes a long time. Certain embodiments can bridge this gap. This semi-robotic system has a fixed-axis system controlled by a locking mechanism to allow the surgeon to easily lock the tools in place as needed throughout the procedure. No longer will they require assistance from additional personnel or from an expensive robot to hold tools. By implementing minimal training upfront, this will decrease the overall cost and fully optimize the procedures being performed, protecting the patient from any damage caused by unwanted movement.

Embodiments can include a new trocar design and a locking mechanism on a fixed-axis system. The trocar exhibits a ball-and-slots style layout. By adding a slotted ball in the center that deflects when the braking system activates, both the trocar and the tool are able to lock their translation and rotation. The slots allow for clamping of the tool/trocar combination by the actuator so that the system can be locked in any three dimensional orientation. Controlling the locking and unlocking feature is a foot pedal wired to the motor. The user simply presses down to engage the foot pedal to lock and again to unlock when ready.

Embodiments provide a laparoscopic surgery tool capable of locking axes of movement on command in a practical way that enhances laparoscopic surgical procedures. Embodiments can toggle the free motion of all axes of motion on the tool being used by the surgeon. Embodiments can lock the free movement and rotation of the tool in 3D space in a practical manner that can aid the operation process. Upon surgeon input, this locking of axes can be toggled on for no movement or off for surgeon-controlled movement of the tools. Embodiments can distribute pressure onto the patient well enough to eliminate the need for excessive volumetric carbon dioxide flow rate into the body. Embodiments can be disposable at a reasonable cost of replacement or have the ability to be sterilized for reuse with traditional medical disinfectants and cleaners.

Certain embodiments utilize a one piece custom trocar (e.g., trocar 103 as disclosed above) featuring a ball-and-slot design. The trocar can sit on top of a port (e.g., disk shaped port 101a) which can be situated on top of the patient. Attached to the port is a linear actuator (e.g., 115) with a brake (e.g., brake 113) that, when engaged, can compress the ball on the trocar, in turn compressing the tool inside and preventing both the trocar and the tool inside from moving while maintaining their position in space. As many trocars (and therefore ports) can be needed for a procedure, they can be connected by a flexible arm system and connected to a rail on the operating table for stability.

Embodiments allow the surgeon to freeze the tool and trocar in 3D space. A ball-and-slots design for the joint on the trocar can include as many slots (e.g., eight, twelve, or any other suitable number, e.g., less than 12) as desired and be made of a suitable material (medical grade metal or plastic) to obtain a suitable deflection when acted upon by the linear actuator. ABS plastic can be utilized for the port and/or trocar and/or any other suitable component, e.g., due to its biocompatibility and the fact that it can be 3D printed (which can be used to make any suitable components disclosed herein). Any suitable material is contemplated herein. By reducing the number of slots on the trocar ball to eight, the strength of the trocar was increased to resist breaking while keeping a low required force to compress the joint. The linear actuator can be connected to a brake pad (e.g., the second clamp member 113b) which can distribute the force around the circumference of the slotted ball and contribute to more even compression.

Figure 3B:
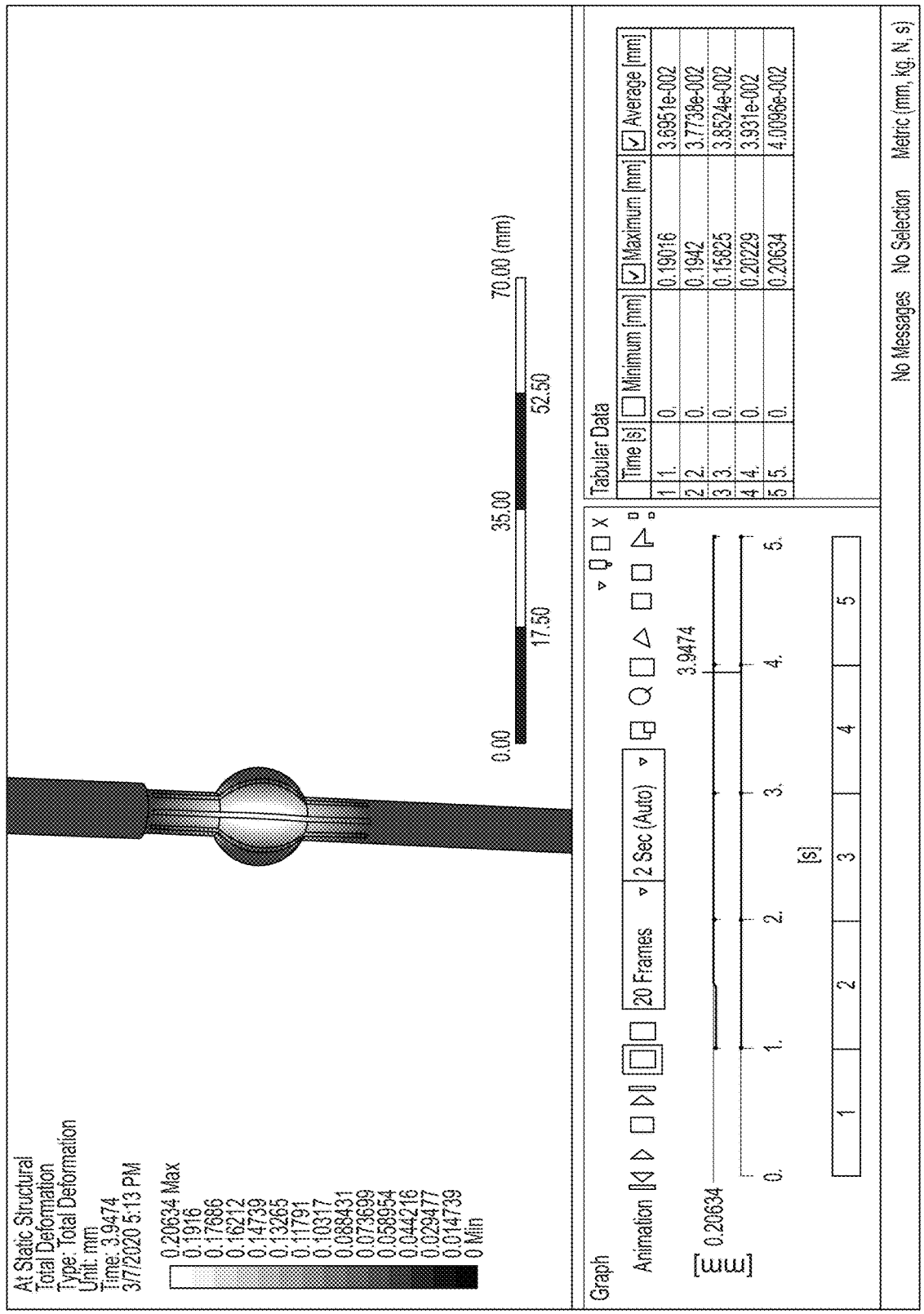
FIG. 3B shows deflection data of the embodiment of FIG. 3A.

The SolidWorks CAD model, as shown in FIG. 3B, was loaded in Ansys where Static Structural simulations were used to verify the force needed to produce a deflection of 0.2 mm. The total deformation plot is captured in FIG. 3B. The 0.2 mm deflection can be important because that can be the amount of space inside the ball of the trocar that is needed to make contact with the tool during surgery. The plot shows that 0.2 mm of deflection occurs in between the fourth and fifth time step, which correlated to 52 N. This meant that, for such an embodiment, the actuator chosen should support more than 52 N to prevent running a device at full power continuously, which constitutes a shorter lifespan and higher maintainability cost. The stress produced by this deflection was also monitored, ensuring to keep it under the yield stress of the material, which is approximately 2,891 psi.

With the patient's stomach inflated with carbon dioxide, it is vital that they do not experience any large force that can irritate their stomach. Therefore, embodiments can be lightweight. For example, the size of the trocar can be the same diameter and length of the traditional trocar, about 7 mm and about 154 mm, respectively (or any other suitable size). However, the ball-and-slots feature that was added to the center of the design can have a diameter of about 15 mm (or any other suitable size). Relevant design parameters and considerations can include the force applied from the actuator, range of motion of the trocar/tool combination, and the pressure of the inflated abdomen. The range of values pertaining to each parameter are approximately 20-50 N, 130°, and 15 mmHg, respectively.

Embodiments can include a tool holder such that the laparoscopic device will lock tools when activated by user. Embodiments can include a braking system that will lock tools in place when desired by user. Embodiments can be such that when the device is engaged by user, braking mechanism will be initiated or terminated. Embodiments can include suitable ergonomics such that the device can follow relevant safety guidelines as defined by Occupational Safety and Health Administration (OSHA).

Embodiments can include a range of motion configured to meet individual patients' body geometry, a power supply to power locking mechanism, and be configured to not harm the user or any individual involved. Embodiments can use materials approved for human-use. Embodiments can fixate to patient to allow for manipulation of tools.

Embodiments can be compatible with current tools, use materials already used in medical field, adhere to patient (adhesives/grip), lock tools in 3D space at current orientation, break under a specified force applied, respond to surgeon input, connect all ports on fixed access, meet safety requirements of operating room (i.e. emergency yield), be transfigured for variations between procedures, be a modular design to allow for reusable or disposable component, be commercially available around the world, be less expensive than robotic laparoscopic surgery, be manufacturable and maintainable around the world, be easy to clean and disinfect, have materials used compatible with disinfectants and cleaners used in operating room, lock/unlock within 5 seconds, and be able to distribute its weight to maintain pressure in the abdomen without changing the volumetric flow rate of carbon dioxide flow into the body.

Embodiments can include a rubber sleeve disposed over the trocar to contain $CO_2$ for surgery. Alternate material considerations for trocar fabrication are contemplated herein. Embodiments can include a coating of biocompatible material (e.g., on the port or any other suitable component).

Embodiments include a Semi-Robotic Laparoscopic Support System for use in minimally invasive surgery to aid doctors with stabilization and assistance of laparoscopic tools. Embodiments of a system can hold tools and trocars in place when the surgeon is not using them, allowing more control over the operation without needing extra workers around the table. Embodiments bridge the gap between requiring several pairs of hands and robotic control. This system can be quick and easy to use, and can include an intuitive foot pedal array and a simple light indication display. Embodiments can also use intelligent braking, stopping motion of both tool and trocar in any configuration without fear of them snapping.

Embodiments can include a method for motor installation. The method can include opening motor housings on the multi-port system, placing motors into each housing, aligning the wires and brake pad, and replacing housing tops. The method can include plugging the three motors into the three-prong cables, plugging the system cord into the system inputs on both the pedal array and the three-port system, and plugging the power cord into the power input on the pedal array.

Certain embodiments can include an arm attachment to fix the system to the surgery table. The arm can help with stability and can alleviate some weight from the patient. The method can include screwing in the surgery table attachment to the three-port system, sliding the other end of the surgery table attachment onto the railing of the surgery table, then tightening with the hand screw. The configuration can be adjusted by unlocking the joints then locking them in the desired position.

Embodiments can be fitted with flexible arms to allow adjustment for varied trocar locations. A method can include determining the trocar locations first before placing the system on the patient. A method can include laying the system on patient, inserting the first trocar, first through one of the ports, then into the abdomen, inflating patient, determining the sites of the other two ports, and placing the other two trocars. Once the trocars and tools are in place, a user can simply perform the surgery as usual. Whenever the user wants to hold a tool in place, they can push on the corresponding foot pedal. The tool will then stay in place until desired. When a locked tool is needed, a user can place a hand on it and push the corresponding foot pedal, and it will become unlocked.

Embodiments can include three LED indicators, one on each arm of the three-port system. The lights can be green, red, or flashing yellow to let a user know what the status of that trocar and tool is. Green can indicate that a respective brake is unlocked such that the brake is not applied, and the tool can move freely. Red can indicate that a respective brake is locked such that the brake is applied, and the tool is fixed in its current position. Flashing yellow can indicate that the system is in the process of either locking or unlocking the tool and that the user should keep a hand on the tool until the light has stopped flashing.

A method for post-surgical removal can include unlocking all trocars and tools one by one, and removing them, unplugging the system from the wall, then unplugging the system cord and the power cord from the unit, if applicable, unscrewing the surgery table attachment arm from the table, sliding it off, then unscrewing from three-port system, and removing the three-port system from patient and remove pedal array from floor.

In certain embodiments, some of the parts must be removed and disposed of, while others can be sterilized and used in surgery again. A method for sterilization can include disposing of the trocars, unplugging the motors and removing them from their housings on the three-port system to dispose of the motors, replacing the plastic caps on three-pronged wires and the system cord entry point of the three-port system, replacing the plastic caps on the power cord and system cord, replacing the plastic caps on the foot pedal array, and sanitizing the three-port system, power cord, system cord, foot pedal array, and (if applicable) the surgery table attachment. Sanitation can be done normally as the other tools and devices. Certain embodiment can be used approximately 50 times before it is recommended that you replace it. The motors and trocars can be be disposed of after each use.

Embodiments can be utilized with great benefits in less equipped medical facilities such as military and rural/small hospitals. For example, embodiments can be utilized in developing/underdeveloped countries where da Vinci robot is not accessible. Any other suitable use or benefit is contemplated herein.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A laparoscopic surgery support system, comprising:
   a plurality of ports configured to receive a trocar therethrough, wherein one or more of the plurality of ports include:
      a body,
      a trocar aperture defined through the body and configured to receive the trocar; and
      a brake configured to hold the trocar in a position relative to the body, wherein the brake is configured to be selectively engaged and disengaged by a user, wherein the brake includes a first clamp portion and a second clamp portion configured to compress a portion of the trocar; and
   a plurality of arms connecting the plurality of ports together and configured to allow fixation of a relative position of the plurality of ports.

2. The system of claim 1, wherein the plurality of ports includes three or more ports.

3. The system of claim 1, wherein the plurality of arms includes multilink arms.

4. The system of claim 3, wherein the multilink arms include a holding force of about 10 kg or greater.

5. The system of claim 1, further comprising an input configured to receive a user command to actuate the brake to selectively hold the trocar.

6. The system of claim 5, wherein the input is a foot pedal or a voice command device.

7. The system of claim 1, further comprising one or more of the trocars configured to be engaged by the brake.

8. A laparoscopic surgery port, comprising:
   a body;
   a trocar aperture defined through the body and configured to receive a trocar; and
   a brake configured to hold the trocar in a position relative to the body, wherein:
      the brake is configured to be selectively engaged and disengaged by a user; and
      the brake includes a first clamp portion and a second clamp portion configured to compress a portion of the trocar.

9. The port of claim 8, wherein the first clamp portion is fixed to the body and wherein the second clamp portion is moveable relative to the body.

10. The port of claim 9, wherein the first clamp portion and the second clamp portion are configured to compress a joint disposed on the trocar.

11. The port of claim 8, further comprising an electric motor configured to actuate the brake.

12. The port of claim 8, wherein the brake is mechanically activated.

13. A trocar, comprising:
   a trocar tube; and
   a joint integrally connected to and/or forming part of the trocar tube, wherein the joint is configured to be compressed by a brake of a laparoscopic surgery port, and wherein the joint includes one or more radially outwardly extending slits extending from the trocar tube and configured to flex.

14. The trocar of claim 13, wherein the joint is shaped to create a ball and socket joint with the port to allow the trocar to rotate in the port.

15. A trocar, comprising:
a trocar tube; and
a joint integrally connected to and/or forming part of the trocar tube, wherein the joint is configured to be compressed by a brake of a laparoscopic surgery port, and wherein the joint is shaped to create a ball and socket joint with the port to allow the trocar to rotate in the port.

* * * * *